us008658187B2

United States Patent
Khan et al.

(10) Patent No.: US 8,658,187 B2
(45) Date of Patent: Feb. 25, 2014

(54) COSMETIC POWDER BEAD COMPOSITIONS

(75) Inventors: Raheel Khan, Franklin Park, NJ (US); Donald Slade, Kinnelon, NJ (US); Marsha C. Dawkins, New Rochelle, NY (US)

(73) Assignee: Avon Products Inc., New York, NY (US)

( * ) Notice: Subject to any disclaimer, the term of this patent is extended or adjusted under 35 U.S.C. 154(b) by 345 days.

(21) Appl. No.: 12/974,688

(22) Filed: Dec. 21, 2010

(65) Prior Publication Data

US 2011/0159060 A1  Jun. 30, 2011

Related U.S. Application Data

(60) Provisional application No. 61/291,246, filed on Dec. 30, 2009.

(51) Int. Cl.
*A61K 8/02* (2006.01)

(52) U.S. Cl.
USPC ............................ 424/401; 424/400; 514/951

(58) Field of Classification Search
USPC .......................................... 424/401; 514/951
See application file for complete search history.

(56) References Cited

U.S. PATENT DOCUMENTS

| | | | |
|---|---|---|---|
| 4,867,984 | A | 9/1989 | Patel |
| 5,026,560 | A | 6/1991 | Makino et al. |
| 6,207,174 | B1 | 3/2001 | Hineno et al. |
| 6,309,655 | B1 | 10/2001 | Minnix |
| 2005/0288478 | A1 | 12/2005 | Burgo |
| 2008/0159804 | A1 | 7/2008 | Brown |

FOREIGN PATENT DOCUMENTS

| | | |
|---|---|---|
| EP | 0983038 B1 | 3/2006 |
| WO | 03/055453 A1 | 7/2003 |
| WO | 2007/089337 A2 | 8/2007 |

OTHER PUBLICATIONS

Ouhlanha et al., "Wet granulation: the effect of shear on granule properties", Powder Technology, vol. 130 (Issue 1-3), pp. 238-246 (2003).*

Iveson et al., "Nucleation, growth and breakage phenomena in agitated wet granulation processes: a review", Powder Technology, vol. 117 (Issue 1-2), pp. 3-39 (2001).*

Oulahna et al.; Wet Granulation: The effect of shear on granule Properties. Powder Technoloy. Feb. 19, 2003, vol. 130, Issue 1-3, pp. 238-246; abstract only [online] http://www.sciencedirect.com/science.

Iveson et al.; Nucleation, Growth and breakage phenomena in agitated wet granulation processes: A review. Powder Technology, Jun. 4, 2001, vol. 117, Issue 1-2, pp. 3-39; abstract only [online] http//www.sciencedirect.com science.

* cited by examiner

*Primary Examiner* — Daniel Sullivan
*Assistant Examiner* — Barbara Frazier
(74) *Attorney, Agent, or Firm* — David M. Joyal; Joan M. McGillycuddy

(57) ABSTRACT

Provided herein are beads comprising at least one structuring agent and least one powder, and a novel process for making same. In one aspect, the process includes solubilzing at least one structuring agent with a solvent in the presence of at least one powder under turbulent high shear mixing to form small, nonspherical nucleated seeds of about 3 mm or less in diameter, and thereafter allowing the nucleated seeds to accrete under laminar low shear mixing to obtain substantially spherical beads of a desired size.

39 Claims, No Drawings

COSMETIC POWDER BEAD COMPOSITIONS

TECHNICAL FIELD

The present disclosure relates to the cosmetic arts, particularly powder bead compositions and to the preparation of the same. Specifically, it relates to a novel process that forms powder beads of a pre-determined desired size and uses thereof.

BACKGROUND

Typically, powder cosmetics may be in the form of loose powders or in a pressed powder compact. The loose powder or compact powder products are generally applied by means of a brush or other applicator by the consumer, although they can also be applied by rubbing the skin with fingertips. Loose powders are easy to apply and have high payoff because they do not contain heavy binders. However, they can be inconvenient to carry and messy to apply because of their low bulk density. Additionally, loose powders are expensive to ship and warehouse because of their high bulk volume.

A pressed powder (or compact powder) comprises pigments and fillers in powder form, and also includes one or more binders such as one or more oils or waxes that allow the mixture of pigments and fillers to be compressed within small trays. Whereas, although compact powders may be more convenient in terms of their packaging, storage and use, compact powders have low payoff, i.e., the ability to transfer the composition from the cosmetic compact to the applicator brush. Additionally, the compact powders are prone to drying out over time resulting in cracking. Compact powders are also prone to breaking, in particular when the cosmetic compact is subjected to strong impact, e.g., by dropping the compact.

Bead cosmetics are also known. Such known beads contain pigments, fillers, and fatty binders, and are made by extruding a pasty mixture of a fatty emulsion and powders at high pressure. See, e.g., WO 03/055453. Such beads are spherical in shape and tend to be harder than the pressed powders due to the high extrusion forces that are applied during manufacture, thereby reducing the payoff even more than the pressed powders. A known extruded bead is Arabian Glow Pearls sold by Avon Products, Inc. Cosmetic beads obtained through this extrusion process must contain additional ingredients such as for example waxes or fatty binders for structure. The method of preparing the conventional beads known in the art are time consuming, labor intensive, and expensive. These extruded conventional beads, which require a fatty component to permit extrusion, cannot claim to contain, for example 100% minerals. Because the extruded beads are hard, they exhibit low payoff, which some consumers find unattractive.

Therefore, there is a need for cosmetic beads that have a compact shape obtained without pressure compaction or paste extrusion as known in the art for pressed powders and that avoid the difficulties and inconveniences of loose powders.

It is an object of the disclosure to a obtain a highly efficient, fast and reproducible process to obtain beads or bead compositions which have the versatility of a loose powder but the convenience of a compact form.

It is another object of the disclosure to provide natural, irritant free translucent or colored beads that provide an even, sheer, and natural-looking coverage when topically applied. This is not possible in the traditional pressed powders due to the binders that are necessarily incorporated.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

SUMMARY

The present disclosure generally relates to beads, bead compositions, and methods of preparing beads and cosmetic or skin care compositions comprising the beads. In particular, the beads comprise at least one structuring agent and at least one powder, where the structuring agent is a gum, a clay, or a synthetic structuring polymer and the powder is any useful ingredient in powder form. The powder may be cosmetically or pharmaceutically acceptable adjuvants and/or excipients selected from but not limited to fillers, powdered colorants such as pigments, lakes and pearls, powdered binders, skin modifiers, active agents, and the like, or compatible combinations thereof.

It is an object of the disclosure to manufacture beads of varying diameters. The disclosed beads are less dense, lighter, and have greater payoff than conventional beads.

Another object is to provide a powder bead having a diameter of about 3 mm or to about 30 mm obtained by the process herein disclosed.

Still another object is to provide a homogeneous powder bead having a diameter of about 3 mm or to about 30 mm whose composition comprises at least one structuring agent, at least one powder, and preferably a liquid binder.

It is one object of the disclosure to provide a process for making the homogeneous powder beads comprising solubilizing at least one structuring agent with a solvent in the presence of at least one powder under turbulent high shear mixing conditions to form nucleated seeds, and thereafter allowing the nucleated seeds to accrete under laminar, i.e., low shear, mixing to obtain the beads of a pre-determined desired size.

Another object of the invention is to utilize a mixing chamber to manufacture the beads of the present disclosure, the mixing chamber being characterized by the ability to provide turbulent high shear initially followed by laminar low shear. In one embodiment the mixing chamber is a granulator, and in particular a vertical granulator.

A further object is to charge the granulator with a powder composition that will allow the beads to form in the granulator in a substantially spherical manner, in accordance with the process as described herein.

Yet another object is to provide a process in which the all or a portion of the solubilized structuring agent is introduced into the mixing chamber, in particular a vertical granulator, as an atomized spray during the turbulent high shear mixing step.

These and other objects of the present disclosure will become apparent to those skilled in the art after a reading of the following detailed description, including the illustrative embodiments and examples.

DETAILED DESCRIPTION

Embodiments of the disclosure are directed to beads and bead compositions comprising at least one structuring agent and at least one powder, uses thereof, and methods of making the beads and bead compositions. Some of the advantages of the disclosed beads when compared to beads in the art that are prepared by paste extrusion are, but not limited to, decreased density, decreased weight, and increased payoff. These advantages are particularly useful from a performance and manufacturing perspective. Moreover, the novel process of making the beads of the present invention allows a bead composition that may contain up to 100% mineral components, e.g., a clay structuring agent and a pigment powder.

As used herein, a "bead" (also "cosmetic bead" or "powder bead") means a finished bead obtained by the novel process herein disclosed, unless otherwise indicated to the contrary. With regard to the composition of the bead, the percentages of the components present in the finished bead are by weight of the finished bead, i.e., following the drying step or after the bead has reached an equilibrium volatiles content, unless otherwise indicated.

As used herein, a "seed" (also "nucleated seed" or "nucleate") means small granules having a diameter of not more than 3 mm obtained during the turbulent high shear mixing step of the novel process and prior to the initiation of laminar shear.

Beads

In one embodiment, the beads comprise at least one structuring agent and at least one powder. Another embodiment is directed to beads comprising at least one structuring agent, at least one powder, and at least one liquid binder. The structuring agents of the disclosure include gums, clays, and synthetic structuring polymers, and combinations thereof. Non-limiting examples of structuring agents include gums such as xanthan gum, guar gum, cellulose gum, sclerotum gum, hydrolyzed gum, carrageenan, sodium carrageenan, gum arabic, cellulosics such as hydroxyethyl cellulose, hydroxyethyl methyl cellulose, hydroxypropyl cellulose, croscarmellose, methylhydroxyethyl cellulose, carboxymethyl cellulose, dextrin, cellulose gum, hydroxypropyl guar, hydroxypropyl chitosan, maltodextrin, gellan gum, carboxymethyl chitosan, alginates such as calcium alginate, carboxylated gum; clays such as hectorites, bentonites, montmorillonites, smectites, magnesium aluminum silicates such as Veegum, illites, chlorites, kaolins, Fuller's earth, and diatomaceous earth; synthetic structuring polymers, including acrylic copolymers, ethylene oxide block polymers, propylene oxide block polymers, polyvinylpyrrolidone copolymers, polycarboxylates, and the like; and compatible combinations thereof. The structuring agent of the disclosed bead may contain at least one structuring agent. The structuring agent generally comprises from about 0.1 to about 10%, preferably from about 0.15 to about 1%, and most preferably from about 0.25 to about 0.5% by weight of the finished bead composition. In various embodiments the structuring agent is present in an amount of 0.1%, 0.2%, 0.3%, 0.4% 0.5% 0.75% and 1%. In one embodiment the structuring agent comprises a mixture of at least one gum and at least one clay. The gums and clays in the structuring agent mixture being in the weight ratio of from about 10:1 to about 1:10, preferably from about 5:1 to about 1:5, and most preferably from about 5:1 to about 1:2. In various embodiments the ratio of gum to clay in the powder bead is 5:1, or 4:1, or 3:1, or 2:1, or 1:1, or 1:2, or 1:3. The preferred gums are cellulose, xanthan gum, and guar gum, and mixtures thereof. The preferred clays are hectorite, bentonite and magnesium aluminum silicate, and mixtures thereof.

The powder or powder phase of the disclosure may be any powder or Powders, such as but not limited to, one or more fillers, powdered colorants including pigments, lakes and pearlescents, powdered binders, powdered skin modifiers, active ingredients in powder form, and the like, and compatible combinations thereof. As used herein the term powder refers to components of the bead product that have a particle size of less than 200 microns. Powders in aggregate may comprise from about 75 to about 99.9% by weight of the finished bead composition, more typically from about 80% to about 99.8%, preferably from about 85 to about 97.5%, and more preferably from about 85 to about 95%. In some embodiments the powders in aggregate comprise 98%, 96%, 94%, 92%, 90%, 88%, 86%, and 84% by weight of the finished bead composition.

Suitable fillers include but not limited to talc, mica, sericite, corn starch, and the like. Fillers are typically present in an amount of from about 0 to about 90%, preferably from about 40 to about 80%, and most preferably from about 50 to about 75%, by weight of the finished bead composition. Additional information on fillers is provided in the section "Additives/Ingredients".

Suitable pigment powders are pigments, lakes, and pearlescents. Pigments include tin oxides, ferric salts, chromium salts, titanium oxides, ultramarines, titanium dioxides, ferrocyanides, ferric ferrocyanides, and iron oxide pigments in black, brown, red, yellow. Suitable pearlescents include nacre, mica-based pearls, synthetic fluorophlogopite-based pearls, and the like. Pigment powders are preferred. Suitably, the pigment and lake powders are typically present in an amount of from about 0 to about 90%, preferably from about 10 to about 50%, and most preferably from about 20 to about 40%, by weight of the finished bead composition. Additional information on pigment powders is provided in the sections "Additives/Ingredients".

Suitable powdered binders may be selected from the group consisting of: metal salts of fatty acids, for example, stearates such as zinc stearate, calcium stearate, aluminum stearate, lithium stearate, magnesium stearate, and myristates such as zinc myristate aluminum myristate, magnesium myristate, or the like; high melting point waxes that are suitable for milling into particulate form, e.g., having a melting point of 60° C. and above such as microcrystalline wax, ozorkerite, polyethylene wax, and the like; polyethylene; methacrylates such as methyl methacrylate, polymethyl methacrylate, or the like; kaolin; lysine derivatives such as lauroyl lysine; boron nitride; fatty alcohols such as cetyl alcohol, stearyl alcohol, eicosanol, or the like; and bismuth oxychloride, and combinations thereof. Powdered binders are typically present in an amount of from about 0 to about 40%, preferably from about 1 to about 20%, and most preferably from about 5 to about 10%, by weight of the finished bead composition. Additional information on binders is provided in the section "Additives/Ingredients".

Suitable skin modifiers include bismuth oxychloride, nylon powder, polyethylene, polymethyl methacrylate, silica, alumina, sterilized silk powder, boron nitride, and the like. Typically, skin modifiers are typically present in an amount of from about 0 to about 90%, preferably from about 1 to about 20%, and most preferably from about 2 to about 10%, by weight of the finished bead composition. Additional information on skin modifiers is provided in the section "Additives Ingredients".

Suitable active agents include allantoin and hyaluronic acid. An active agent is generally present in an amount effective to achieve its intended function. Active agents are typically present in an amount of from about 0 to about 10%, preferably from about 0.001 to about 5, and most preferably from about 0.1 to about 1, by weight of the finished bead composition. Additional information on active agents is provided in the section "Additives Ingredients".

In one embodiment, the powder beads comprise at least one structuring agent, at least one powder, and further comprise additional ingredients, such as but not limited to at least one liquid binder.

One purpose of the at least one liquid binder is to facilitate the accretion process, as hereinafter described. Moreover, the liquid binder also provides structure to the bead, reduces crumbling and friability that could result in damage to the product during shipping and use, and improves powder deposition onto an applicator as well as to the skin of the consumer.

Non-limiting examples of liquid binders include polyols such as low molecular weight glycols including propylene glycol, butylene glycol, and pentalene glycol, glycerin, low molecular weight polyol derivatives such that these are in liquid form, examples of which include but are not limited to polyethylene glycol, dipentaerythrityl hexa $C_5$-$C_9$ acid esters and the like. In certain embodiments, if liquid binders are used, then powdered binders may not be necessary. However, if powdered binders are used, then in preferred embodiments a liquid binder is also included. Generally the liquid binders are present in an amount ranging from about 0% to about 25%, preferably from about 2 to about 15%, and most preferably from about 5 to about 10% by weight of the finished powder bead. If included, the liquid binder, which is not volatile, will substantially remain in the final bead product. Typically, the liquid binders have a vapor pressure of less than 0.1 mm Hg at 20° C.

The finished beads of the invention will contain residual solvent, typically water, notwithstanding a drying step to remove most of the solvent. The amount of solvent remaining in the beads is less than about 10% by weight of the finished bead product, typically less than about 5% by weight. More volatile solvents will of course be present in lower amounts, with water tending to be higher, and dependent on atmospheric humidity conditions.

Method of Preparing Beads

Another embodiment of the disclosure is directed to the preparation of the beads. The process for making the homogeneous powder beads comprises solubilizing at least one structuring agent with a solvent in the presence of at least one powder under turbulent high shear mixing conditions to form small, typically nonspherical nucleated seeds, and thereafter allowing the nucleated seeds to accrete under laminar low shear mixing to obtain the beads of a pre-determined desired size. While optional, the beads are then preferably dried in to remove substantially all of the solvent or to establish an equilibrium solvent concentration.

In one embodiment the structuring agent, powders, and any additional ingredients of the bead, e.g., liquid binder, are admixed under conditions of turbulent high shear, during which step the solvent is atomized into the admixture, followed by laminar low shear mixing until the beads attain their desired diameter, and then drying the beads.

In another embodiment the structuring agent, solvent, and powders are admixed under conditions of turbulent high shear, followed by laminar low shear mixing until the beads attain their desired diameter, and then drying the beads. Preferably, the structuring agent and solvent are first formed into a premix to solubilize the structuring agent, following which the powders are admixed.

In a preferred embodiment the structuring agent and solvent are first formed into a premix, a portion of the premix, together with the powders and any additional ingredients, e.g., liquid binder, being admixed under conditions of turbulent high shear, with the remainder portion of the premix being concurrently atomized thereinto, during which turbulent high shear nucleated seeds are form of less than 3 mm. Following the formation of the seeds, the mixture is admixed under conditions of laminar low shear, which allows the beads to form and attain their desired diameter. Optionally, the beads are then dried.

The solvent is particularly a volatile solvent, such as, but not limited to a polar solvent including water, or a low molecular weight alcohol such as isopropyl alcohol or ethanol. The solvent, the structuring agent, and the at least one powder are admixed at high turbulence having a high shear rate and tip speed. One embodiment of the method occurs by atomizing a solvent phase onto a powder phase. The atomized solvent phase comprises at least one solvent and optionally the at least one structuring agent. In one embodiment, the structuring agent may be in the atomized solvent phase in any amount that is uniformly dissolved by the solvent and yet remains atomizable. The solvent is particularly useful as a volatile solvent that can uniformly and completely dissolve the structuring agent. The solvent also is sufficiently present to swell the structuring agent. Both components are present in amounts sufficient to atomize the solvent phase.

Without wishing to be bound by theory, the solvent phase uniformly, especially when atomized with structuring agent into the granulator, saturates the powders and forms a uniform coating of structuring agent on the powders while under turbulent high shear flow. As the powders saturate, liquid bridges are believed to form, and the high circular shear of the granulator results in the formation of nucleated seeds. The turbulence limits these nucleated seeds to a diameter of from about 1 to about 3 mm, more typically about 2 mm. When laminar shear commences, accretion of the nucleated seeds occurs to form beads. The amount of solvent phase, shear rate during the laminar shear step, and mixing time determines the size, uniformity, and shape of the beads as the nucleated seeds begin to accrete. The skilled formulator or practitioner will of course take care to choose the parameters in such a way that the desired or advantageous properties of the beads and their applications result.

In a typical embodiment, the beads prepared by the methods disclosed herein utilize a solvent Phase A where the solvent ranges from about 90% to about 100% by weight and the structuring agent ranges from 0% to about 10% by weight. Powder Phase B comprises fillers ranging from 0 to about 95%, preservatives in an amount ranging from 0% to about 5%, pigment powders in an amount from 0% to about 80%, and liquid binders in an amount ranging from 0% to about 25% by weight. The weight ratio of the solvent Phase A to the powder Phase B is typically from about 1:1 to about 1:10, preferably from about 1:2 to 1:8, and more preferably from about 1:3 to about 1:6.

In the preferred embodiment Phase A comprising the structuring agent and the solvent is divided, a portion of which is atomized into the mixing chamber/granulator, and the other portion of which is combined with the powder Phase B. Typically, 25 to about 75%, more typically with about 40 to about 60% of the total solvent Phase A is combined with the powder Phase B. Nonetheless, Phase B as so modified remains in powder form. The remainder of the solvent Phase A is atomized into the mixing chamber/granulator under conditions of turbulent high shear.

Mixing of the solvent Phase A, and the powder Phase B, which comprises at least one powder and optionally, but preferably, a portion of solvent Phase A, occurs using any known mixers that rotate circularly with a blade that can achieve both turbulent and laminar flow. Suitably, a vertical granulator is used, for example, a commercially available unit manufactured by Glatt GmbH (Model #: FM VG 65 M). The vertical granulator is equipped with a main blade and a chopper blade to turbulently admix the powder Phase B (as may be modified by incorporating a portion of the solvent Phase A) and the portion of solvent Phase A to be atomized under high shear/tip speed in an essentially circular path causing the structuring agents and the powder constituents to form nucleated seeds. Once the mixing is reduced to low shear/tip speed laminar flow or shear, the nucleated seeds accrete over time into essentially spherical beads. The diameter of the beads present in the granulator increase, and by modifying parameters, the final size of the bead can be predetermined.

In one embodiment, the solvent phase is atomized and sprayed onto the powder phase while mixing under turbulent flow. Initially, in order to form nucleated seeds which are necessary as the foundation of the beads of varying sizes, the ingredients are mixed at a high shear rate and tip speed of greater than about 15 ft/s to maintain turbulent flow. More specifically, the solvent phase and powder phase are mixed in a vertical granulator at a speed of about 150 rpm to about 450 rpm that results in a tip speed of about 15 ft/s to about 41 ft/s, or about 16 ft/s to about 30 ft/s. The skilled artisan understands that the time to form nucleated seeds having a diameter of about 1 mm to about 3 mm generally ranges from about 20 minutes to about 30 minutes, but may vary depending on the atmospheric conditions. For example, on particularly humid days, additional mixing time may be necessary and/or the addition of more powder phase, while on dry days, less mixing time may be necessary and/or the addition of more solvent phase. However, one of ordinary skill in the bead composition art understands how to adjust for the varying conditions.

One particular embodiment is directed to mixing the powder phase while atomizing the solvent phase comprising the structuring agent solubilized in solvent onto the powder under conditions of high turbulence, high shear and high tip speed to form nucleated seeds of about 1 mm to about 3 mm in diameter. In another embodiment, about half of the solvent phase is mixed with the powder phase, and the remaining half of the solvent phase is atomized onto the powder phase, all under high turbulence, high shear, and high tip speed to form non-spherical nucleated seeds of about 1 mm to about 3 mm in diameter. Turbulent flow is considered to have a tip speed of greater than about 15 ft/s and during this time the powders are being mixed in a random turbulent flow. Generally, under high turbulence, nucleated seeds or beads having a diameter of about 1 mm to 3 mm, generally less than 2 mm are formed. These nucleated seeds are the foundation of the final beads and due to the nature of the turbulence, the nucleated seeds cannot grow uniformly in size.

Another embodiment is directed to obtaining beads, typically having a diameter ranging from about 2 mm to about 30 mm. Therefore, after the nucleated seeds have formed under high shear, turbulent flow, the mixing speed is reduced to low shear, laminar flow which has a tip speed of less than about 15 ft/s to allow for the accretion of the nucleated seeds. Only under low shear, laminar flow and low tip speed can the nucleated seeds grow into larger beads by uniformly coating the nucleated seeds and/or multiple nucleated seeds binding together to ultimately form a bead having a diameter of about 2 mm to about 30 mm. As is understood in the art, the faster the shear rate or tip speed, the smaller the bead size. By adjusting the parameters, the skilled artisan can obtain the desired final bead size. Additionally, the components of the beads, i.e., powder pigments, whiteners, anti-aging agents, etc., dictate the final composition.

After achieving the desired bead size, the beads may optionally be coated with a clean uniform layer of powder in order to obtain visually aesthetically pleasing round, uniform and shiny beads. An additional benefit of the late stage powder coating is to further facilitate the halt in bead size growth.

In one embodiment, a final step of the disclosed method, i.e., after bead formation, is directed to drying the beads by any means known in the art. More specifically, after the bead has reached the desired predetermined size, the beads are removed from the vertical granulator for final processing. Typically, especially when a volatile solvent has been utilized during the atomized solvent phase preparation, the beads are dried to remove the volatiles. Drying may be achieved by any of the numerous different commercial methods. In so doing, substantially all remaining solvent will be removed. Non-limiting examples of drying methods include, baking, forced hot air, convection, and the like. Although any drying technique may be used in the disclosed method, forced air at a temperature of about 80° C. for 2 to 6 hours is particularly useful, depending on the nature and amount of volatiles to be removed.

Another embodiment where at least one liquid binder is utilized in the disclosed beads, the drying step does not substantially remove the at least one liquid binder. Liquid binders are useful in maintaining the integrity of the beads, and are acceptable in the final bead product since they are non-volatile. Generally, the composition of the beads is essentially similar to the powder phase including any structuring agent to the granulator, less volatiles that evaporate during processing. The final beads following the drying step, or when the beads reach an equilibrium solvent content in air, contain less than about 10% volatiles, and preferably less than about 5 weight % volatiles.

A further embodiment of the disclosure is directed to any atomizer that sufficiently sprays the solvent phase comprising at least one structuring agent solubilized in solvent onto the powder phase. The granulator used in the disclosed method is equipped with a spray nozzle manufactured by Spraying Systems Company (¼ LNN SS#3). Air at a pressure of about 50 psi to about 100 psi may be necessary to force the solvent phase through a nozzle that results in the solution being atomized and sprayed evenly on and wetting the powders homogenously so they become saturated and liquid bridges begin to form.

The rate at which the atomized solvent phase saturates the powder phase is about 0.5 gm/s to about 3.5 gm/s and depends on the types of powders, binders and liquids used. Once the powder phase reaches saturation under turbulent flow, nucleated seeds of a small diameter size, typically about 1 to about 3 mm, are produced. After nucleation, the bead size of the final product is controlled by adjusting the tip speed, the mixture times, and/or the amount of additional solvent. The more solvent present and the lower the shear rate resulting from lower tip speeds, the more the seeds will try to attach to each other and grow. Consequently, increasing the shear rate by increasing tip speed results in the beads to break off and become smaller in size.

In one embodiment, the diameter of the beads, formed by agglomerating the nucleated seeds, ranges from about 1 mm to about 30 mm, or about 3 mm to about 20 mm, or about 5 mm to about 10 mm that results from mixing under laminar flow at a tip speed of about 10 ft/s to about 15 ft/s for about 10 minutes to about 30 minutes. In other embodiments the beads have a diameter of 4 mm, of 5 mm, of 10 mm, of 15 mm, and of 20 mm. The homogeneous beads of the desired size that are formed have the versatility of a loose powder but the convenience of a compact form without any of the disadvantages of prior art beads that are formed by extruding a paste, such as but not limited to, prior art beads of high density, weight, and friability which must be forced and extruded under pressure to obtain a compact form.

In one embodiment, the beads are characterized by a weight/diameter ratio of less than beads obtained by the extruded paste process. More specifically, the disclosed beads have a weight/diameter of less than about 0.034 g/mm and an average weight/diameter of about 0.031 g/mm. The beads are further characterized as having particularly good payoff which is demonstrated by any improvement over the art, i.e., an improvement of greater than about 10%, greater than about 25%, greater than about 50%, greater than about 100%, and greater than about 200%. Example 4 and Table 4 show that the disclosed beads have over a 240% payoff.

Bead Parameters

After turbulent flow and the formation of nucleated seeds, the accretion of the nucleated seeds result in final bead diameters ranging from about 2 mm to about 30 mm depending on the desired application. A useful bead diameter ranges from about 4 mm to about 8 mm. However, larger beads may be desirable. Table 1 discloses the parameters during laminar low shear/tip speed, i.e., after nucleation, in order to obtain the final bead diameters. The % Solvent added refers to those embodiments where no bead growth is observed, then additional solvent, such as water, may be added.

These are general parameters, as the skilled formulation artisan understands that a faster tip speed results in smaller bead sizes or diameters, while slower tip speeds results in larger bead sizes or diameters. The mixing time is inversely proportional. Specifically, if a small bead size is desired, then a shorter mixing time is required; whereas, if a large bead size is desired, a longer mixing time is desired. Furthermore, the more solvent used in the method of preparing the beads results in larger beads because more powder is saturated by more solvent, and combined with the low tip speed and long mixing time, essentially the bead grows by having a lot of uniform coats that result in the beads becoming tacky and wanting to attach to one another. The skilled practitioner or formulator understands the parameters that are necessary to prepare homogeneous beads for the appropriate application.

TABLE 1

| BEAD SIZE (mm) | TIP SPEED (ft/s) | MIXING TIME (min) | MAX % SOLVENT ADDED | TOTAL % SOLVENT |
|---|---|---|---|---|
| 2-4 | 12-17 | 4-12 | 0-2 | 20-25 |
| 4-8 | 10-15 | 8-18 | 0-5 | 22-28 |
| 8-16 | 7-13 | 10-30 | 0-7 | 24-31 |
| 16-30 | 7-13 | 10-45 | 0-12 | 24-34 |

Additives/Ingredients

The powder phase may include colorants or pigments such as but not limited to pearlescent compounds, iron oxides, tin oxides, ferric salts, manganese salts, chromium salts and titanium oxides, ultramarines, titanium dioxides, titanium dioxides on mica, ferrocyanides, ferric ferrocyanides, ferric ammonium ferrocyanides, carmines, manganese violets, iron oxide pigments in black, brown, red, yellow, drug and cosmetic grade organic colors, blue 1 lakes, red 40 lakes, yellow 5 lakes, yellow 6 lakes, chromiums, chromium hydroxide greens, chromium oxide greens, synthetic fluorphlogopite, and the like, or combinations thereof.

The powder phase may comprise of powdered binders. Non-limiting examples of powdered binders include metal salts of fatty acids, zinc stearates, aluminum stearates, calcium stearates, lithium stearates, magnesium stearates, high melting point waxes that can be milled into particulate form, for example microcrystalline and polyethylene waxes, typically having a melting point 60° C. and above and in particular above about 75° C., polyethylenes, methacrylates, methyl methacrylates, polymethyl methacrylates, kaolins, lauroyl lysines, boron nitrides, fatty alcohols, acetyl alcohols, stearyl alcohols, eicosanols, bismuth oxychlorides, and the like, or combinations thereof. While hydrophobic binders are to be limited, the powder phase may contain up to about 5%, and more preferably not more than about 1% by weight of the finished powder bead. Hydrophobic binders include, e.g., waxes and esters in solid form.

Powdered skin modifiers useful in the beads include but are not limited to silica powders, nylon powders, extra fine nylon powders, polymethyl methacrylates, polyvinylidene copolymers, barium sulfates, silicas, aluminas, sterilized silk powder, polyethylenes, boron nitrides, and the like, or combinations thereof.

The powder phase may comprise at least one powder of a powdered active agent. The powdered actives may include but are not limited to antifungal agents, analgesics, antipruritics, antimicrobials, antpsoratics, antibiotics, antiperspirants, UV protectants, antioxidants, antiaging ingredients such as dried botanical extracts, microdermabrasives, allantoin, hyaluronic acid, and the like or combinations thereof. Silicone oils may also be incorporated into the powder phase in low levels, generally less than about 5&, in particular less than about 1% by weight of the finished powder bead, as a feel modifier for the final product. The active ingredient is present in the bead in an amount effective to provide its intended effect, typically ranging within about 0.001% to about 10% by weight, preferably in an amount ranging from about 0.01% to less than about 1 weight %.

In certain embodiments, preservatives may be used in the beads or bead compositions of the present disclosure. They include, but are not limited to, methyl paraben, butyl paraben, propyl paraben and phenoxyethanol.

Due to consumer demand for a more youthful appearance or the desire to delay aging, antioxidants are often used in cosmetics. The beads or bead compositions of the present disclosure may also comprise antioxidants such as but not limited to butylated hydroxy anisole (BHA) and butylated hydroxy toluene (BHT).

Emollients may also be useful in the beads or bead compositions of the present disclosure. They include any emollients known in the cosmetic arts, such as but not limited to, octyl palmitate and triisocetyl citrate. For all of the ingredients useful in the disclosure, alternatives may include any of those known in the art and/or listed in the *International Cosmetic Dictionary and Handbook*. (Eds. Gottschalck, Tara E., and Gerald N. McEwen. Twelfth ed. Washington, D.C.: The Cosmetic, Toiletry, And Fragrance Association (Now Known As The Personal Care Products Council), 2008), the contents of which are hereby incorporated by reference.

Applications

In one embodiment the cosmetic product is a plurality of homogeneous powder beads provided in a suitable container, to be used as a substitute for pressed powders, loose powders, and the known extruded beads. The beads may range in diameter from about 3 to about 30 mm. These beads may have colorants or may be translucent. Each bead may have a single color or a plurality of colors. A cosmetic product containing these beads may comprise a number of beads having a plurality of colors, which may be packaged separately within the container for the beads. For example, in one embodiment, the beads may each have a slightly varying color of bronze, where some beads may be darker than others. The collection of these beads forms a cosmetic bronzing composition for topical application to the face or body.

In a further embodiment, the instant disclosure is directed to a composition comprising the beads in a carrier; the beads typically having a diameter of less than about 5 mm. The carrier, vehicle, or diluent, collectively referred to herein as carriers, depends on the desired application. The beads may be used with a carrier to form a skin care composition or a colored cosmetic composition, where the beads provide an anti-wrinkling, anti-aging active or colorants, respectively.

Yet a further specific embodiment is directed to the beads where the powder is a colorant, such as for example, an organic or inorganic colorant. The homogeneous powder beads may be applied directly to the skin or may be incorporated into a gel or cream for application to the skin. More specifically, the gel or cream comprising the homogeneous powder beads is the carrier. For example, the gel or cream may be a clear or translucent composition comprising the homogeneous beads which form a cosmetic composition for topical application. As is understood in the art, these types of applications of the colored beads give rise to color cosmetics applicable for application to the eyes, face and lip areas.

A further embodiment of the disclosure is directed to the homogeneous beads which comprise an active ingredient which is beneficially protected until the desired time for release. In one embodiment, beads comprising zeolites, which are useful for removing toxins, free radicals and ions, may be applied to a specific location on the consumer, such as the face. The zeolites may be entrapped in the beads and released once the beads are squeezed or ruptured by the consumer.

In yet another example, the beads may be useful in any application in which a powder is desired or useful. Non-limiting examples of various applications of the beads include facial or body powders, blushes, eyeshadows, eyeliners, and the like.

For those cosmetic compositions comprising the disclosed beads and a carrier, the carrier may be a composition in the form of a gel, cream, lotion, or the like. Alternatively, non-limiting examples of carriers useful in combination with the beads of the disclosure may include: any known in the art suitable for application to skin and may include water (e.g., deionized water); vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, dimethicone, dimethicone cross-polymer, polysiloxanes and their derivatives, preferably organomodified derivatives; hydrocarbon oils such as mineral oil, petrolatum, isoeicosane and polyisobutene; polyols such as propylene glycol, glycerin, butylene glycol, pentylene glycol and hexylene glycol; waxes, typically low melting, i.e., less than about 60° C., such as beeswax and botanical waxes; or any combinations or mixtures of the foregoing.

More specifically, the carrier, vehicle, or diluent may comprise an aqueous phase, an oil phase, an alcohol, a silicone phase or mixtures thereof. The cosmetically acceptable vehicle may also comprise an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. The emulsion may include an emulsifier, such as a nonionic, anionic or amphoteric surfactant. Additional carriers are provided in the *INCI Ingredient Dictionary and Handbook* 11th Edition 2006, the disclosure of which is hereby incorporated by reference.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this disclosure can be made without departing from its spirit and scope, as will be apparent to those skilled in the art. The specific embodiments described herein are offered by way of example only, and the disclosure is to be limited only by the terms of the appended claims, along with the full scope of equivalents to which such claims are entitled. As used herein, the term "consisting essential of" is intended to limit the invention to the specified materials or steps and those that do not materially affect the basic and novel characteristics of the claimed invention, as understood from a reading of this specification.

The following example(s) further describes embodiments of the present disclosure, but are not limiting nor departing from the scope of this invention. In the Examples that follow, the percentages for each of the phases, e.g., Phase A, are by weight of the components of that phase, unless otherwise indicated.

EXAMPLES

Example 1

Colored Bead Composition

Table 2 provides one exemplary colored bead composition. Briefly, the bead was prepared by mixing the ingredients of Phase B together to form the powder phase, followed by processing in a hammer mill. Phase A, or the solvent phase, was prepared by mixing the structuring agent in the solvent while mixing under high shear for about 30 minutes to allow the structuring agent to solubilize. The amount of structuring agent added in Phase A is determined by the viscosity of Phase A which should not increase more than about 64,000 cP, as this makes Phase B too thick for atomization through the nozzle of the vertical granulator identified below. Any remaining structuring ingredients that may be needed for the structure of the bead composition end product may be added to the Phase B powder phase.

The Phase B powder phase was added to the vertical granulator (# FM VG 65 M; Glatt GmbH) running at high main blade speed and high chopper blade speed. The solvent Phase A was added to the powder Phase B at about 2 g/s under high speed mixing. Table 1 presents an exemplary formulation of the solvent phase and the powder phase.

TABLE 2

| INGREDIENT | AMOUNT (%) |
|---|---|
| Phase A: | |
| Solvent | 99.38 |
| Structuring Agent(s) | 0.62 |
| Phase B: | |
| Fillers | 65.12 |
| Preservatives | 0.77 |
| Colorants | 27.75 |
| Structuring Agents | 0.36 |
| Liquid Binders | 6 |

Example 2

General Method of Preparing Powder Beads

The vertical granulator (Glatt or Fluid Air) that was previously equipped with a spray nozzle (¼ LNN SS#3). The powder Phase B was added to the granulator and mixed for about 1 minute using a speed of 250 rpm for the main blade and 2500 rpm for the chopper blade. About 50% of the solvent Phase A dispersion was added into a spray kettle and pressurized to 60 psi and sprayed onto the powder Phase B. The addition of the solvent Phase A took approximately 10 minutes until all of the liquid was forced out of the spray lines and nozzle. After spraying, the tank was opened and the walls and blades were scraped down, such that the solvent Phase A was uniformly distributed.

All of the contents were mixed with a main blade speed of 250 rpm and chopper blade speed of 2500 rpm. The remaining solvent phase, i.e., ~50%, was added and sprayed at a pressure of about 60 psi taking about 10 minutes. Once again, after all of the liquid was forced out of the spray lines and nozzle, the tank was opened and the walls and blades were scraped down to ensure that nothing remained on the interior surfaces of the granulator. At this point, if there were no beads or beads smaller than 1-3 mm, and instead the ingredients were primarily on the interior surfaces, water would be added (no more than 1% of the batch weight for each increment added) while mixing at a speed of 250 rpm main blade and 2500 rpm chopper blade. The addition of each increment was spaced over 2 minutes of mixing. Once the batch had the proper appearance or texture, the batch was mixed for another 3 minutes at 150 rpm main blade and 1500 rpm chopper blade speeds until the beads reached the desired size, i.e., ~3 mm to 30 mm.

If, however, no growth was observed, i.e., agglomeration of nucleated seeds, then water was added (no more than 1% of the batch weight for each increment added) and mixed at 150 rpm main blade speed and 1500 rpm chopper blade speed until the beads reached the desired size. During the addition of the water, mixing occurred for 3 minutes for each increment. Once the final desired size was reached, the copper blade was removed and the beads were mixed for 2 minutes at 150 rpm main blade speed and 500 rpm chopper bar (without blade) speed to allow the beads to become round and uniform. When about 90% of the beads reached the desired size, they were mixed for additional 2 minute intervals at 100 rpm main blade speed to round the beads and make them appear uniform. Finally, an additional 1% of the batch weight of powder was added and mixed for 1 minute at 125 rpm main blade speed to have a smooth, round, and shiny surface of the bead. These beads are then emptied in trays and placed in a forced air heat oven for 4 hours at 80 C to drive the water from the beads.

Example 3

Property Differences from that of Extruded Beads

The disclosed beads that are prepared by the method of Example 2 differ from conventional beads produced by extrusion. Generally, the disclosed beads are less dense and lighter, and yet have a better payoff than the extruded beads.

Table 3 shows the bead diameters and bead weights for 6 exemplary extruded beads (Ex Beads) and 6 exemplary beads as disclosed (D Beads). The average Extruded bead had a bead diameter of 6.19 mm, 0.27 g, and weight to diameter ratio of 0.0349 g/mm. Whereas, the average Disclosed bead had a bead diameter of 6.21 mm, 0.20 g, and weight to diameter ratio of 0.0313 g/mm.

It was calculated that the Extruded bead has a weight/diameter ratio of 11.5% more than the Disclosed bead even though the bead diameter were approximately the same. The density of the Extruded bead also is greater than the Disclosed bead by 11.3%. Since the Disclosed bead is packed less tightly than the Extruded bead that is in the prior art, a bead that is about the same size but that weighs less than the Extruded beads of the art, results in a final bead product that is more than 10% lighter than the customary beads of the art and therefore the disclosed beads cost less.

TABLE 3

|  | Weight (g) | Diameter (mm) | Weight/Diameter Ratio (g/mm) |
| --- | --- | --- | --- |
| EXTRUDED BEADS: |  |  |  |
| Ex Bead 1 | 0.27 | 6.70 | 0.0403 |
| Ex Bead 2 | 0.22 | 6.18 | 0.0356 |
| Ex Bead 3 | 0.19 | 5.90 | 0.0322 |
| Ex Bead 4 | 0.22 | 6.18 | 0.0356 |
| Ex Bead 5 | 0.21 | 6.23 | 0.0337 |
| Ex Bead 6 | 0.19 | 5.96 | 0.0319 |
| Average Ex Bead | 0.22 | 6.19 | 0.0349 |
| DISCLOSED BEADS: |  |  |  |
| D Bead 1 | 0.21 | 6.73 | 0.0312 |
| D Bead 2 | 0.16 | 5.62 | 0.0285 |
| D Bead 3 | 0.21 | 6.29 | 0.0334 |
| D Bead 4 | 0.20 | 6.30 | 0.0317 |
| D Bead 5 | 0.22 | 6.50 | 0.0338 |
| D Bead 6 | 0.17 | 5.83 | 0.0292 |
| Average D Bead | 0.20 | 6.21 | 0.0313 |

Example 4

Comparison of Payoff of Beads

In order to measure the benefit of payoff of the beads of the disclosure compared to the extruded beads of the prior art, an individual bead was taken and applied on a smooth area of skin having a surface area of about 8 cm$^2$ by rubbing or moving the bead back and forth on the skin for 50 strokes. The weight of the bead before and after application was measured to calculate the amount of payoff. After measuring the weight before and after 50 strokes, the loss of mass of each of 6 Extruded beads (Ex Bead) of the prior art and 6 Disclosed beads (D Bead) were calculated as shown in Table 4. The average Disclosed Bead Loss/average Extruded Bead Loss ratio was calculated to be 2.42. The Disclosed bead had a surprisingly large increase in payoff that was 242% more than the payoff of the Extruded bead.

TABLE 4

| Beads | Loss of Mass Upon 50 Strokes (g) |
| --- | --- |
| EXTRUDED BEAD: |  |
| Ex Bead 1 | 0.0032 |
| Ex Bead 2 | 0.0035 |
| Ex Bead 3 | 0.0033 |
| Ex Bead 4 | 0.0036 |
| Ex Bead 5 | 0.0026 |
| Average Extruded Bead | 0.00324 |
| DISCLOSED BEAD: |  |
| D Bead 1 | 0.0095 |
| D Bead 2 | 0.0084 |
| D Bead 3 | 0.0065 |
| D Bead 4 | 0.0096 |
| D Bead 5 | 0.0053 |
| Average Disclosed Bead | 0.00786 |

Example 5

A powdered bead formulation of the present invention is illustrated below. The Phase A particulate components set forth in Table 5.1 are mixed together to form the powder phase, followed by processing in a hammer mill. The Phase B solvent phase components set forth in Table 5.2 are prepared by mixing solubilizing the gum structuring agent in the water solvent by mixing under high shear for about 30 minutes. As indicated in the Detailed Description of the Invention, not all of the structuring agent recited in Table 5.2 may be used in the preparation of Phase B, as the viscosity of Phase B should remain sufficiently low for it to be atomized into the nozzle of the vertical granulator identified below. Any remaining structuring ingredient that may be needed for the structure of the bead composition end product is added to the Phase A powder phase.

TABLE 5.1

| Phase A components (Powder Phase) | Amount (Wt. %) |
| --- | --- |
| Fillers | |
| Mica | 79.50 |
| Preservatives | |
| Methylparaben | 0.40 |
| Propylparaben | 0.20 |
| Powder Binders | |
| Polyethylene-12 micron | 2.50 |
| Colorants | |
| Iron oxide (mix of black, red and yellow) | 3.40 |
| Pearlescents (iron oxide and titanium dioxide coated micas) | 7.50 |
| Liquid Binders | |
| dipentaerythrityl hexa C5-9 acid esters | 4.00 |
| Hydrogenated Castor Oil | 2.50 |
| Total Phase A components | 100.0 |

TABLE 5.2

| Phase B components (Solvent Phase) | Amount (Wt. %) |
| --- | --- |
| Water | 99.38 |
| Gum blend (xanthan, hectorite and cellulose) | 0.62 |
| Total Phase B components | 100.00 |

The Phase A powder phase is added to the vertical granulator (# FM VG 65 M; Glatt GmbH) running at high main blade speed and high chopper blade speed. The solvent Phase B is atomized into the powder Phase A at about 2 g/s under high speed mixing to create seeds as described herein. Processing in the vertical granulator continues until beads of the desired size are obtained.

Example 6

A powdered bead formulation of the present invention is illustrated below. The Phase A particulate components set forth in Table 6.1 are mixed together to form the powder phase, followed by processing in a hammer mill. Water is the Phase B solvent phase component as set forth in Table 6.2. Any structuring ingredients in this example are added in the powder phase A that may be needed for the structure of the bead composition end product.

TABLE 6.1

| Phase A components (Powder Phase) | Amount (Wt. %) |
| --- | --- |
| Fillers | |
| Mica | 81.93 |
| Gums | 0.30 |
| Preservatives | |
| Methylparaben | 0.40 |
| Propylparaben | 0.20 |
| Powder Binders | |
| Polyethylene-12 micron | 2.00 |
| Colorants | |
| Iron oxide (mix of black, red and yellow) | 3.42 |
| Pearlescents (iron oxide and titanium dioxide coated micas) | 7.50 |
| Liquid Binders | |
| Dipentaerythrityl hexa C5-9 acid esters | 4.00 |
| Sodium polyacrylate-100% | 0.25 |

TABLE 6.2

| Phase B components Solvent Phase | Amount (Wt. %) |
| --- | --- |
| Water | 100.00 |

The Phase A powder phase is added to the vertical granulator (# FM VG 65 M; Glatt GmbH) running at high main blade speed and high chopper blade speed. The solvent Phase B is added to the powder Phase A at about 2 g/s under high speed mixing to create seeds as described herein. Processing in the vertical granulator continues until beads of the desired size are obtained.

Example 7

A powdered bead formulation of the present invention is illustrated below. The Phase A particulate components set forth in Table 7.1 are mixed together to form the powder phase, followed by processing in a hammer mill. The Phase B emulsion phase is in the form of an emulsion and the components are set forth in Table 7.2, which are prepared by mixing the aqueous and disperse phases and the preservatives under high shear at 175° C. The skin modifiers and glyceryl monostearate are mixed together and added at 175° C. into the first mix. This final mixture is then cooled to room temperature. As indicated in the Detailed Description of the Invention, not all of the structuring agent recited in Table 7.2 may be used in the preparation of Phase B, as the viscosity of Phase B should remain sufficiently low for it to be atomized into the nozzle of the vertical granulator identified below. Any remaining structuring ingredients that may be needed for the structure of the bead composition end product is added to the Phase A powder phase.

TABLE 7.1

| Phase A components (Powder Phase) | Amount (Wt. %) |
|---|---|
| Fillers | |
| Mica | 69.58 |
| Sericite | 15.00 |
| Preservatives | |
| Methylparaben | 0.40 |
| Propylparaben | 0.20 |
| Powder Binders | |
| Zinc stearate | 2.50 |
| Colorants | |
| Iron oxide (mix of black, red and yellow) | 3.32 |
| Liquid Binders | |
| Butylene glycol | 6.00 |
| Glycerin | 3.00 |

TABLE 7.2

| Phase B components (Emulsion Phase) | Amount (Wt. %) |
|---|---|
| Aqueous phase | |
| Demineralized water | 81.0 |
| Cyclomethicone-pentamer | 3.00 |
| Carbopol | 0.10 |
| Disperse phase | |
| Glyceryl monostearate | 0.6 |
| Triethanolamine | 0.10 |
| Skin modifier oils | 14.30 |
| Preservative | |
| Imidazolidinyl urea | 0.40 |
| Methylparaben | 0.40 |

The Phase A powder phase is added to the vertical granulator (# FM VG 65 M; Glatt GmbH) running at high main blade speed and high chopper blade speed. The emulsion Phase B is added to the powder Phase A at about 2 g/s under high speed mixing to create seeds as described herein. Processing in the vertical granulator continues until beads of the desired size are obtained.

What is claimed is:

1. A method of preparing powder beads, comprising:
solubilizing at least one structuring agent with a solvent in the presence of at least one powder under turbulent high shear mixing at a tip speed of greater than about 15 ft/s to form small, nonspherical nucleated seeds of about 3 mm or less in diameter, and
thereafter allowing the nucleated seeds to accrete under laminar low shear mixing at a tip speed of less than about 15 ft/s to obtain substantially spherical beads having a diameter of about 3 mm to about 30 mm.

2. The method of claim 1, further comprising drying the beads.

3. The method of claim 1, wherein the turbulent high shear mixing and/or laminar low shear mixing occurs in a vertical granulator.

4. The method of claim 1, wherein said powder comprises at least one liquid binder.

5. The method of claim 4, wherein the liquid binder is selected from the group consisting of glycerin, butylene glycol, and dipentaerythrityl hexa $C_5$-$C_9$ acid esters.

6. The method of claim 5, wherein the liquid binder comprises dipentaerythrityl hexa $C_5$-$C_9$ acid esters.

7. The method of claim 6, wherein the bead has an improved payoff ranging from about 1% to about 300% than extruded beads.

8. The method of claim 1, wherein the structuring agent is a gum, a clay, or a synthetic structuring polymer.

9. The method of claim 8, wherein the gum is an alginate, a hydroxyethyl cellulose, ahydroxyethylmethyl cellulose, a hydroxypropyl cellulose, a carboxymethyl cellulose, a carrageenan, a guar gum, a xanthan gum, a gum arabic, or combinations thereof.

10. The method of claim 8, wherein the clay is a hectorite, a bentonite, a montmorillonite, kaolin, a fuller's earth, a diatomaceous earth, or combinations thereof.

11. The method of claim 8, wherein the synthetic structuring polymer is a polyvinylpyrrolidone, an ethylene oxide block copolymer, a propylene oxide block copolymer, or a polycarboxylate.

12. The method of claim 1, wherein the powder is a filler, a pigment, a powdered binder, a skin modifier, or combinations thereof.

13. The method of claim 12, wherein the filler is talc, mica, sericite, corn starch, and combinations thereof.

14. The method of claim 12, wherein the pigment is an inorganic pigment.

15. The method of claim 14, wherein the inorganic pigment is an iron oxide, a ferric salt, a manganese salt, a chromium salt, a titanium oxide, or combinations thereof.

16. The method of claim 12, wherein the powdered binder is selected from the group consisting of metal salts of fatty acids; waxes; polyethylene; methacrylates; lauroyl lysine; boron nitride; fatty alcohols; bismuth oxychloride, and combinations thereof.

17. The method of claim 16, wherein the powdered binder is selected from the group consisting of zinc stearate, calcium stearate, aluminum stearate, lithium stearate, magnesium stearate, zinc myristate, aluminum myristate, magnesium myristate, microcrystalline wax, polyethylene wax; methyl methacrylate, polymethyl methacrylate, cetyl alcohol, stearyl alcohol, eicosanol, and combinations thereof.

18. The method of claim 12, wherein the skin modifier is silica powder, nylon, or combinations thereof.

19. The method of claim 1, wherein the bead has a weight to diameter ratio of less than about 0.034 g/mm.

20. A method of preparing powder beads, comprising:
solubilizing at least one structuring agent with at least one solvent, forming a solvent phase;
mixing at least one powder under turbulent tip speed greater than about 15 ft/s;
atomizing at least a portion of said solvent phase onto said powder;
mixing the solvent phase and said powder under turbulent flow to form nonspherical nucleated seeds of about 3 mm or less in diameter;
mixing the nucleated seeds under laminar tip speed less than about 15 ft/s to form substantially spherical beads having a diameter of about 3 mm to about 30 mm; and
drying said beads.

21. The method of claim 20, wherein the portion of the solvent phase not atomized onto said powder is combined directly with the powder.

22. The method of claim 20, wherein the turbulent high shear mixing and/or laminar low shear mixing occurs in a vertical granulator.

23. The method of claim 20, wherein the nucleated seeds are nonspherical and have a diameter of about 1 mm to about 3 mm.

24. The method of claim 20, wherein the structuring agent is a gum, a clay, or a synthetic structuring polymer.

25. The method of claim 24, wherein the gum is an alginate, a hydroxyethyl cellulose, ahydroxyethylmethyl cellulose, a hydroxypropyl cellulose, a carboxymethyl cellulose, a carrageenan, a guar gum, a xanthan gum, a gum arabic, or combinations thereof.

26. The method of claim 24, wherein the clay is a hectorite, a bentonite, a montmorillonite, kaolin, a fuller's earth, a diatomaceous earth, or combinations thereof.

27. The method of claim 24, wherein the synthetic structuring polymer is a polyvinylpyrrolidone, an ethylene oxide block copolymer, a propylene oxide block copolymer, or a polycarboxylate.

28. The method of claim 20, wherein the powder is a filler, a pigment, a powdered binder, a skin modifier, or combinations thereof.

29. The method of claim 28, wherein the filler is talc, mica, sericite, corn starch, and combinations thereof.

30. The method of claim 28, wherein the pigment is an inorganic pigment.

31. The method of claim 30, wherein the inorganic pigment is an iron oxide, a ferric salt, a manganese salt, a chromium salt, a titanium oxide, or combinations thereof.

32. The method of claim 28, wherein the powdered binder is selected from the group consisting of metal salts of fatty acids; waxes; polyethylene; methacrylates; lauroyl lysine; boron nitride; fatty alcohols; bismuth oxychloride, and combinations thereof.

33. The method of claim 32, wherein the powdered binder is selected from the group consisting of zinc stearate, calcium stearate, aluminum stearate, lithium stearate, magnesium stearate, zinc myristate, aluminum myristate, magnesium myristate, microcrystalline wax, polyethylene wax; methyl methacrylate, polymethyl methacrylate, cetyl alcohol, stearyl alcohol, eicosanol, and combinations thereof.

34. The method of claim 28, wherein the skin modifier is silica powder, nylon, or combinations thereof.

35. The method of claim 20, wherein the bead has a weight to diameter ratio of less than about 0.034 g/mm.

36. The method of claim 20, wherein the powder comprises at least one liquid binder.

37. The method of claim 36, wherein the liquid binder is selected from the group consisting of glycerin, butylene glycol, and dipentaerythrityl hexa $C_5$-$C_9$ acid esters.

38. The method of claim 37, wherein the liquid binder comprises dipentaerythrityl hexa $C_5$-$C_9$ acid esters.

39. The method of claim 38, wherein the bead has an improved payoff ranging from about 1% to about 300% than extruded beads.

* * * * *